United States Patent
Burgess et al.

(10) Patent No.: US 12,288,618 B2
(45) Date of Patent: Apr. 29, 2025

(54) ELECTRONIC TAGS FOR ASSOCIATING AND IDENTIFYING INTRAVENOUS ADMINISTRATION LINES

(71) Applicant: CareFusion 303, Inc., San Diego, CA (US)

(72) Inventors: Brendan John Burgess, Poway, CA (US); Edward Stephen Ferner, Escondido, CA (US); Beth A. Schneider, San Diego, CA (US); Shannon John Johnson, Doral, FL (US); Daniel M. Abal, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 806 days.

(21) Appl. No.: 17/402,417

(22) Filed: Aug. 13, 2021

(65) Prior Publication Data

US 2022/0051792 A1    Feb. 17, 2022

Related U.S. Application Data

(60) Provisional application No. 63/066,113, filed on Aug. 14, 2020.

(51) Int. Cl.
*G16H 40/67* (2018.01)
*A61M 5/14* (2006.01)
(Continued)

(52) U.S. Cl.
CPC ........ *G16H 40/67* (2018.01); *A61M 5/16854* (2013.01); *G01F 22/02* (2013.01);
(Continued)

(58) Field of Classification Search
CPC .................................................... G16H 20/17
See application file for complete search history.

(56) References Cited

U.S. PATENT DOCUMENTS

| 5,713,856 A | 2/1998 | Eggers et al. |
| 7,256,888 B2 | 8/2007 | Staehr et al. |
| (Continued) | | |

FOREIGN PATENT DOCUMENTS

| EP | 2968746 A1 | 1/2016 |
| WO | WO-2019164988 A1 | 8/2019 |

OTHER PUBLICATIONS

International Search Report and Written Opinion for Application No. PCT/US2021/046051, dated Nov. 16, 2021, 11 pages.
European Office Action for Application No. 21766756.7, dated Mar. 6, 2025, 4 pages.

*Primary Examiner* — Getente A Yimer
(74) *Attorney, Agent, or Firm* — Morgan, Lewis & Bockius LLP

(57) ABSTRACT

An electronic tag includes a housing; a processor within the housing; a transceiver configured within the housing and coupled to the processor; a display coupled to the housing and the processor, and configured to display information received via the transceiver; a clamping mechanism coupled to the housing and configured to secure the electronic tag to an intravenous (IV) tubing; and a sensor configured within the housing, and configured to measure a property of a fluid in an IV tubing at a location of the clamping mechanism.

18 Claims, 10 Drawing Sheets

(51) Int. Cl.
  *A61M 5/168*  (2006.01)
  *A61M 5/172*  (2006.01)
  *A61M 39/08*  (2006.01)
  *G01F 22/02*  (2006.01)
  *G06K 19/07*  (2006.01)
  *G16H 20/17*  (2018.01)
  *G16H 40/40*  (2018.01)
  *G16H 40/63*  (2018.01)

(52) U.S. Cl.
  CPC ......... *G06K 19/0728* (2013.01); *G16H 20/17* (2018.01); *G16H 40/40* (2018.01); *A61M 2205/502* (2013.01)

(56) References Cited

U.S. PATENT DOCUMENTS

| | | | |
|---|---|---|---|
| 7,417,729 | B2 | 8/2008 | Greenwald |
| 7,856,746 | B1 | 12/2010 | Araujo |
| 9,227,025 | B2 | 1/2016 | Butterfield et al. |
| 9,307,907 | B2 | 4/2016 | Condurso et al. |
| 11,160,710 | B1 * | 11/2021 | Augustine .............. G16H 20/17 |
| 11,933,650 | B2 * | 3/2024 | Ruchti .............. A61M 5/16831 |
| 11,938,300 | B2 * | 3/2024 | Freudenthal ........ A61M 5/1415 |
| 2002/0038392 | A1 * | 3/2002 | De La Huerga ....... G16H 20/17 710/8 |
| 2002/0062437 | A1 * | 5/2002 | Shin ..................... G06F 15/177 713/300 |
| 2019/0091398 | A1 | 3/2019 | Utz |

\* cited by examiner

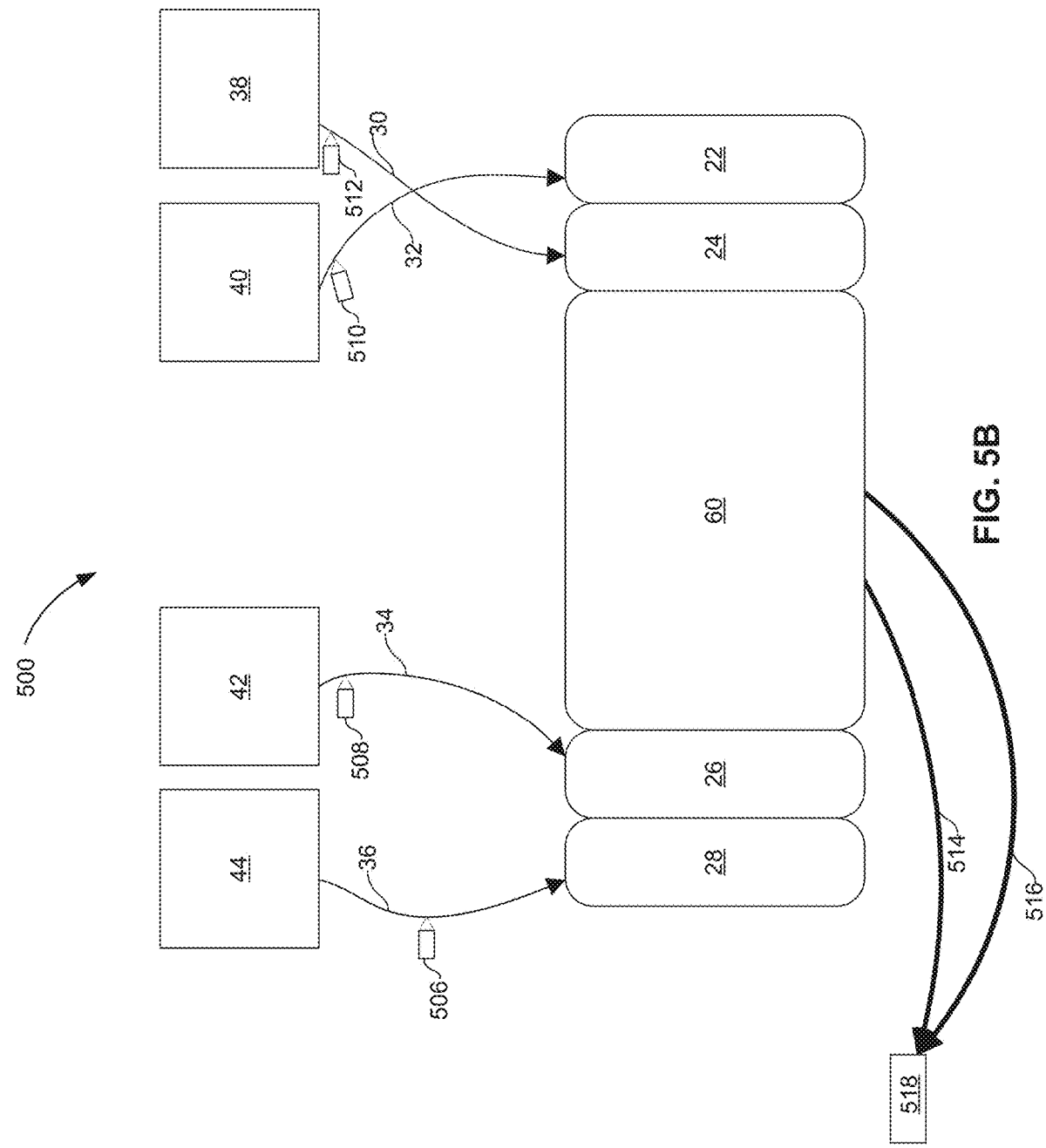

ELECTRONIC TAGS FOR ASSOCIATING AND IDENTIFYING INTRAVENOUS ADMINISTRATION LINES

CROSS REFERENCE TO RELATED APPLICATIONS

This application claims the benefit of U.S. Provisional Application Ser. No. 63/066,113, entitled "ELECTRONIC TAGS FOR ASSOCIATING AND IDENTIFYING INTRAVENOUS ADMINISTRATION LINES," filed on Aug. 14, 2020, the entirety of which is incorporated herein by reference.

TECHNICAL FIELD

This application relates generally to associating and identifying intravenous (IV) administration lines.

BACKGROUND

A patient receiving care in an intensive care units and/or an operating room may be connected to multiple IV administration lines. Ensuring that each administration line is correctly connected to the correct infusion fluid, and delivered to the patient at the correct infusion rate, may require substantial time and labor to track the path of each IV administration line between the patient and a respective infusion pump or fluid container. The presence of more than one IV administration line may lead to risks associated with misconnections or an IV administration line going to an infusion pump that is not programmed at the correct infusion rate for the infusion fluid. Tape or tags may be attached to the lines with written information on what medication container each line is attached. However, tape can fall off, be difficult or unintelligible to read, information recorded incorrectly. For safety reasons, IV administration lines are also monitored to ensure that the use of the IV administration lines does not extend beyond their intended usage period.

SUMMARY

Information relevant to the infusion, such as contents of the fluid container attached to each IV administration line, who initiated the IV administration line, and the date and time the IV administration line started, may be written on tapes or tags and attached to the lines. However, the tape may fall off, be difficult or unintelligible to read, or contain information that is recorded incorrectly.

Labeling and reconciliation of IV lines (a process also known as "line tracing") may be done at least once per shift by a clinician. Line tracing is conducted to ensure that a particular medical fluid is connected to the intended channel for infusion to the intended patient. The clinician may check during line tracing that (i) the IV administration set has not been used beyond its intended usage period (or expired), (ii) the fluid in the fluid container has not expired, (iii) the IV administration line of the IV set is correctly labeled with stickers, (iv) the infusion pump is correctly labeled electronically, and (v) the IV site at the patient is patent. The clinician may record such information as electronic documentation in the patient's electronic medical record (EMR).

Accordingly, there is a need for devices and methods that help to reduce the labor and increase efficiency associated with labeling, and line reconciliation. Such devices and methods may also help to improve the accuracy of expiry information associated with the IV set and/or the infusion medication to be infused that is provided to the clinician. More accurate line reconciliations also prevent accidental line swaps in which the wrong medical fluid is used in the infusion. Accidental line swaps may also cause the correct medical fluid to be infused at the wrong infusion rate through the wrong infusion pump to the patient.

The disclosed subject matter relates to an electronic tag and methods of using the electronic tag to correctly associate an IV container with an IV set. The electronic tag may be programmed to display pertinent information relating to the infusion process, for example, the name of the medical fluid to be infused, the name of the patient, the name of the clinician initiating the infusion, the start time of the infusion, the expiration time of the IV set, and barcode information relating to the infusion that can be used to track and record various steps of the infusion process, track the patient and/or medication, or for other purposes.

The disclosed devices and methods, in addition to tracking and identifying IV lines, also include a sensor that provides real-time feedback regarding whether a particular IV fluid container has been correctly associated with an IV administration set. The sensor can also monitor if the IV fluid container is empty, and send out timely notifications or warning to the clinician.

The disclosed subject matter also relates to a system for associating a fluid container with an infusion pump. The system includes one or more processors and a memory including instructions that, when executed by the one or more processors, cause the one or more processors to perform the steps of the method described herein.

The subject technology provides an electronic tag that includes a housing; a processor within the housing; a transceiver configured within the housing and coupled to the processor; a display coupled to the housing and the processor, and configured to display information received via the transceiver; a clamping mechanism coupled to the housing and configured to secure the electronic tag to an intravenous (IV) tubing; and a sensor configured within the housing, and configured to measure a property of a fluid in an IV tubing at a location of the clamping mechanism. Other aspects include corresponding methods, apparatus, and computer program products for implementation of the corresponding system and its features.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

FIG. 5B is a conceptual diagram illustrating the use of multiple electronic tags.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Figure 1:
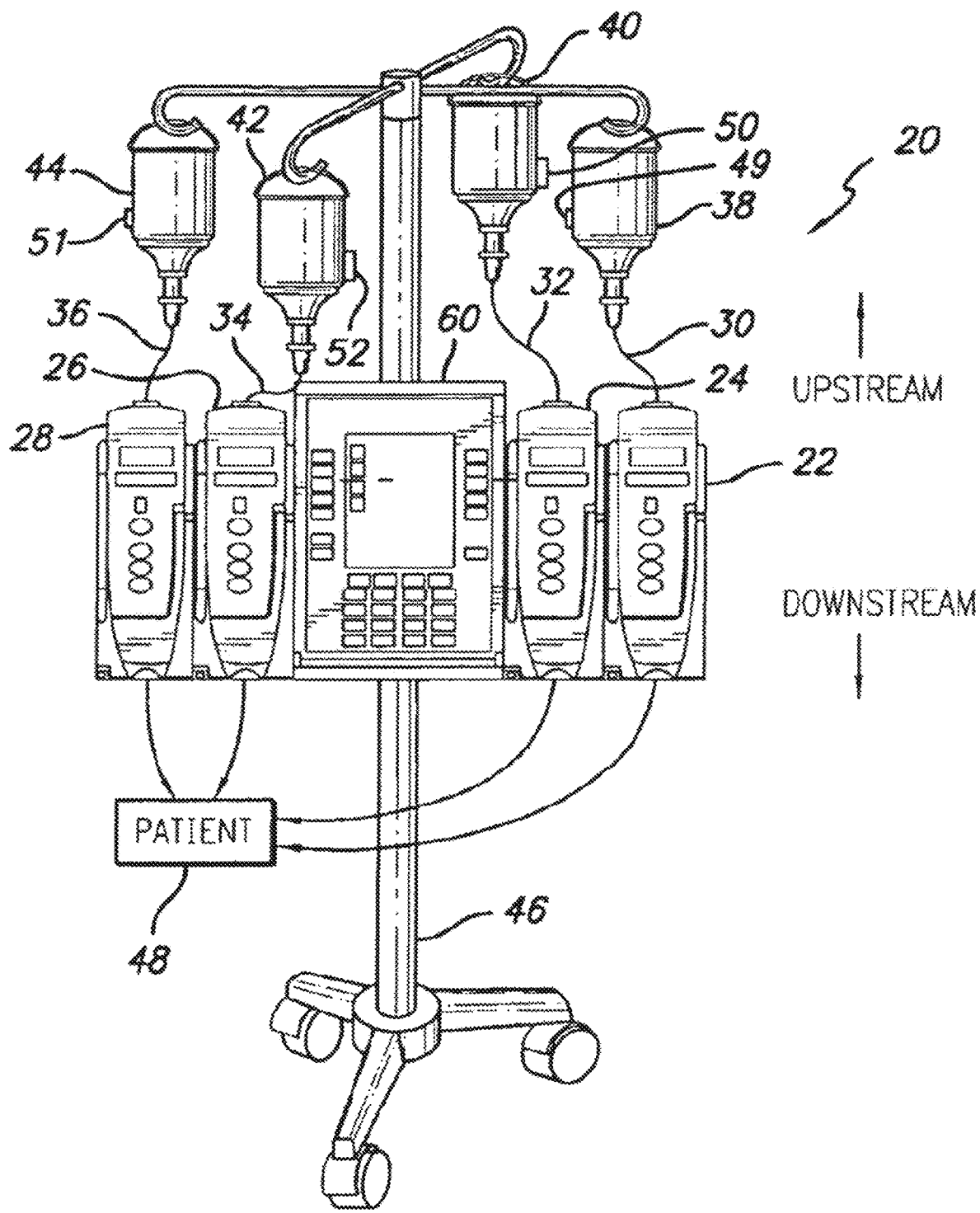
FIG. 1 is a front view of a medical administration system having four fluid infusion pumps, each of which is connected to a respective fluid container for pumping the contents of the fluid container to a patient, the fluid containers being mounted on a common roller stand, according to aspects of the subject technology.

FIG. 1 shows a medical administration system 20 having four medical administration devices 22, 24, 26, and 28, which are infusion pumps in this implementation, each of which is in operative engagement with a respective fluid administration set 30, 32, 34, and 36. Medical fluid supplies or containers 38, 40, 42, and 44, which may take various forms but in this case are shown as inverted bottles, are suspended above the pumps. Fluid supplies may also take the form of bags or other types of containers. Both the infusion pumps 22, 24, 26 and 28 and the fluid containers 38, 40, 42, and 44 are mounted to a roller stand or IV pole 46.

Each administration set 30, 32, 34, and 36 is connected between a respective fluid container 38, 40, 42, and 44 and the same patient 48, so that the patient is connected to multiple fluid administration sets and receives fluids from multiple fluid containers (e.g., four in this example). A separate infusion pump 22, 24, 26, and 28 is used to infuse each of the fluids of the fluid containers into the patient. The infusion pumps are flow control devices that will act on the respective tube or fluid conduit of the fluid administration set to move the fluid from the fluid container through the conduit to the patient. Because individual pumps are used, each can be individually set to the pumping or operating parameters required for infusing the particular medical fluid from the respective fluid container into the patient at the particular rate prescribed for that fluid by the physician. Such medical fluids may include medications, drugs, nutrients, or other therapeutic fluids as previously mentioned.

Typically, medical fluid administration sets have more parts than those shown in FIG. 1. Many have check valves, drip chambers, valved ports, connectors, and other devices well known to those skilled in the art. Sometimes, during the course of an infusion therapy regimen, a second drug is prescribed for infusion at the same time a first drug is being infused into a patient. Attention is directed to U.S. Pat. No. 9,307,907 entitled "System and method for dynamically adjusting patient therapy" to Condurso et al., incorporated herein by reference, in which further details about how secondary infusions may be accomplished using a "Y-Site" connector that provides access to the primary infusion source line are provided. These other devices have not been included in the drawings so as to preserve clarity of illustration. However, those skilled in the art will understand that the inclusion of such other devices may often occur.

In accordance with the background discussed above, it is desirable to verify that each fluid container 38, 40, 42 and 44 is associated with the correct patient 48, that the pumping parameters for a given medical fluid have been correctly programmed into the infusion pump 22, 24, 26 or 28, and that each fluid container is correctly connected to the appropriately programmed pump. As will be discussed in more detail below, the present invention allows an infusion fluid line to be more easily and accurately associated with an infusion device which controls its fluid flow and/or with the fluid container from which the fluid originates. Data devices associated with the medical fluid containers, such as acoustic transducers 49, 50 51, and 52 shown mounted on the bottles, associated with the patient 48, may communicate relevant administration data to the pumps for verifying that the medical administration system 20 has been connected correctly. Relevant administration data may include various data related to the administration of medical fluid to a particular patient. For example, relevant administration data may include drug identification, patient identification, and other information believed to be relevant.

It should be noted that the drawing of FIG. 1 is not to scale and that distances have been compressed and sizes have been exaggerated for the purpose of clarity. In an actual setting, the distance between the containers 38, 40, 42, and 44 and the infusion pump 22, 24, 26, and 28 could be much greater. There would be more of an opportunity for the tubes of the administration sets 30, 32, 34, and 36 to become intertwined with each other when all four are dangling from the containers, which can cause confusion as to which tube should be in which infusion pump. The opportunity for confusion increases as the number of tubes increases. However, it should also be understood that the present invention is also useful in cases where a single pump and single medical fluid container are involved, as the system may also be used to confirm that the correct medication has arrived for the patient and that the infusion parameters have been correctly programmed into the pump.

The terms "upstream" and "downstream" as shown in FIG. 1 and as used herein in various places is meant to provide an indication of relative positioning as well as indicate the positions of certain specific devices. For example, the patient is located "downstream" from the pump and is also "downstream" from the container. The pump is located "upstream" from the patient, as is the container. On the other hand, there is an "upstream data reader device" and a "downstream data reader device"" which denote their relative positions on the pump.

Figure 2:
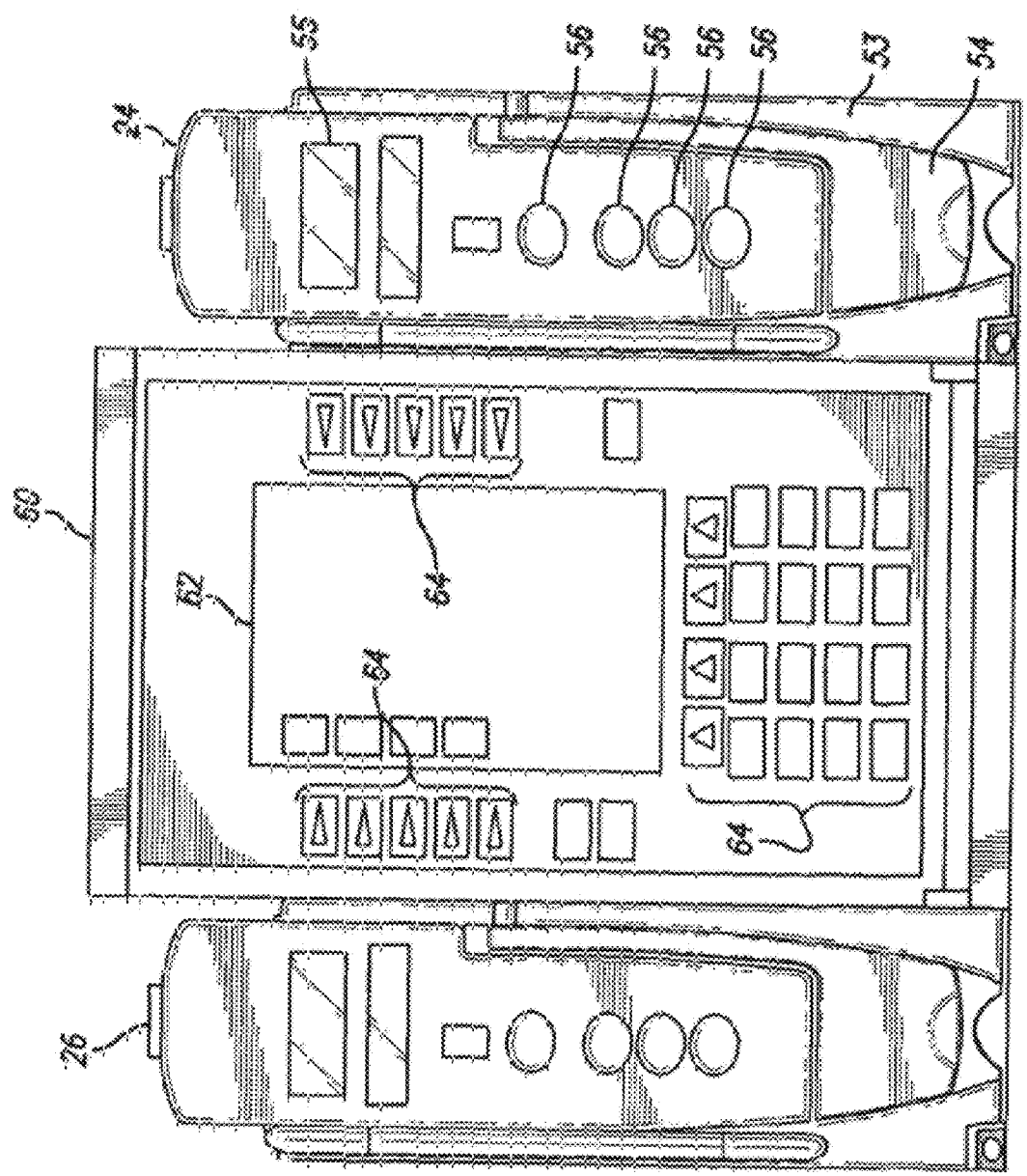
FIG. 2 is an enlarged view of a portion of the medical administration system of FIG. 1 showing two of the fluid infusion pumps mounted at either side of a programming module, and the displays and control keys of each, with the programming module being capable of programming both infusion pumps, according to aspects of the subject technology.

Referring now to FIG. 2, an enlarged view of the front of the infusion pump 24 is shown. The pump includes a front door 53 and a handle 54 that operates to lock the door in a closed position for operation and to unlock and open the door for access to the internal pumping and sensing mechanisms and to load administration sets for the pump. When the door is open, the tube can be connected with the pump. When the door is closed, the tube is brought into operating engagement with the pumping mechanism and the other equipment of the pump. A display 55, such as an LED display, is located in plain view on the door in this embodiment and may be used to visually communicate various information relevant to the pump, such as alert indications (e.g., alarm messages). Control keys 56 exist for programming and controlling operations of the infusion pump as desired. In some implementations, the infusion pump 24 also includes audio alarm equipment in the form of a speaker 58.

In some implementations, as shown in FIG. 2, the infusion pump 24 is attached to the right side a programming module 60. Other devices or modules, including another infusion pump, may be attached to the right side of the infusion pump 24, as shown in FIG. 1. In such a system, each attached pump represents a pump channel of the overall medical administration system 20. In one embodiment, the programming module is used to provide an interface between the infusion pump 24 and external devices as well as to provide most of the operator interface for the infusion pump 24. Attention is directed to U.S. Pat. No. 5,713,856 entitled "Modular Patient Care System" to Eggers et al., incorporated herein by reference, in which the programming module is described as an advanced interface unit. In other cases, the programming module is referred to as a "point-of-care unit."

The programming module 60 includes a display 62 for visually communicating various information, such as the operating parameters of the pump 24 and alert indications and alarm messages. The programming module 60 may also include a speaker (not shown) to provide audible alarms. The programming module also has various input devices in this embodiment, including control keys 64. The programming module also has a communications system (not shown) with which it may communicate with external equipment such as a medical facility server or other computer and with a portable processor, such as a handheld portable digital assistant ("PDA"), or a laptop-type of computer, or other information device that a caregiver may have to transfer information as well as to download drug or medication libraries to a programming module or pump. The communications system may take the form of a RF system, an optical system such as infrared, a BlueTooth system, or other wired or wireless system. The communications system may alternatively be included integrally with an infusion pump, such as in cases where it is a stand alone pump. Further, information input devices need not be hard-wired to medical instruments, information may be transferred through a wireless connection as well.

FIG. 2 includes a second pump module 26 connected to the programming module 60. As shown in FIG. 1, more pump modules may be connected. Additionally, other types of modules may be connected to the pump modules or to the programming module.

Figure 3:
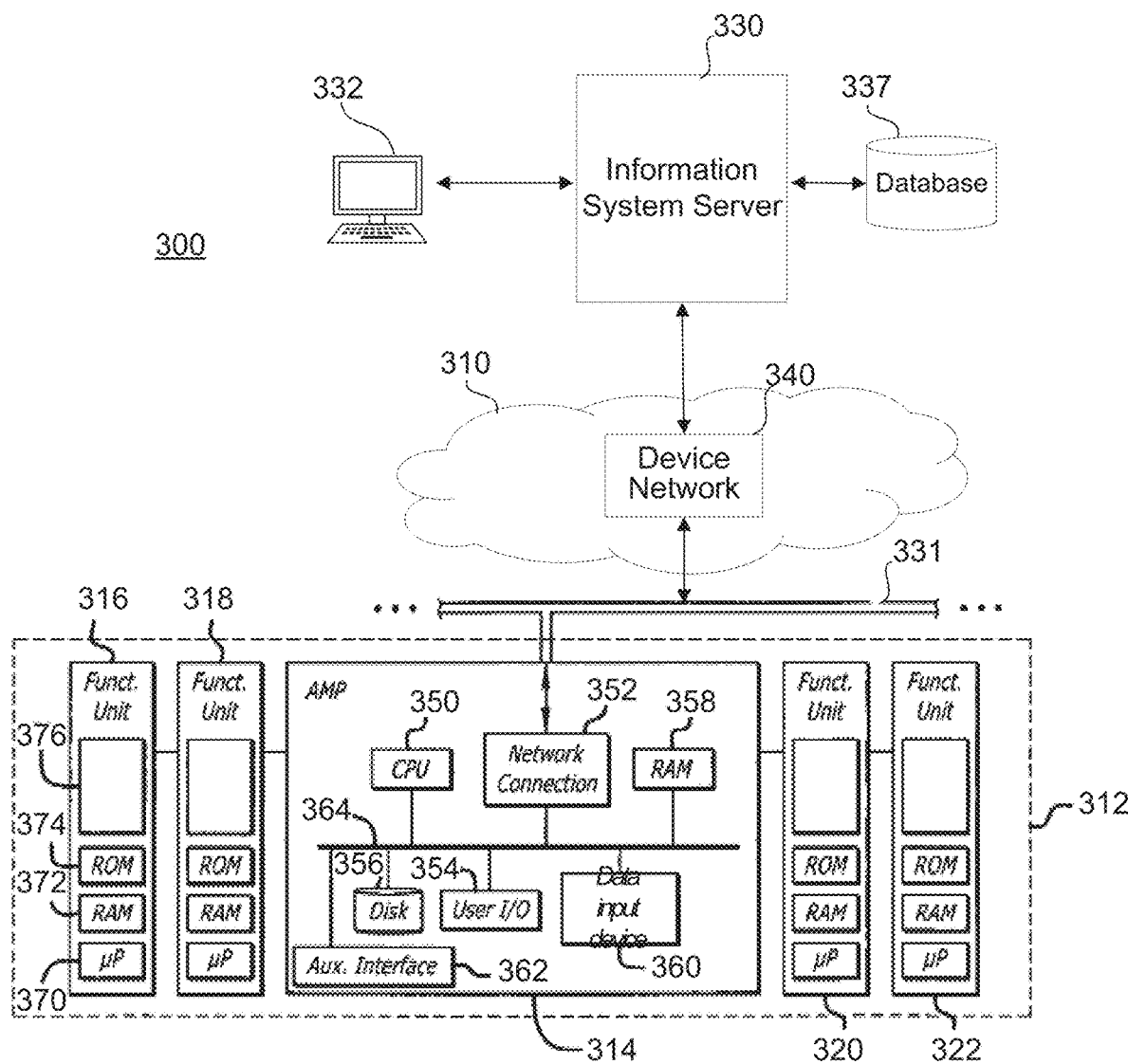
FIG. 3 depicts an example of an institutional patient care system of a healthcare organization, according to aspects of the subject technology.

FIG. 3 depicts an example of an institutional patient care system 300 of a healthcare organization, according to aspects of the subject technology. In FIG. 3, a patient care device (or "medical device" generally) 312 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 312 is connected to an internal healthcare network 310 by a transmission channel 331. Transmission channel 331 is any wired or wireless transmission channel, for example an 802.11 wireless local area network (LAN). In some implementations, network 310 also includes computer systems located in various departments throughout a hospital. For example, network 310 of FIG. 3 optionally includes computer systems associated with an admissions department, a billing department, a biomedical engineering department, a clinical laboratory, a central supply department, one or more unit station computers and/or a medical decision support system. As described further below, network 310 may include discrete subnetworks. In the depicted example, network 310 includes a device network 340 by which patient care devices 312 (and other devices) communicate in accordance with normal operations.

Additionally, institutional patient care system 100 may incorporate a separate information system server 330, the function of which will be described in more detail below. Moreover, although the information system server 330 is shown as a separate server, the functions and programming of the information system server 330 may be incorporated into another computer, if such is desired by engineers designing the institution's information system. Institutional patient care system 300 may further include one or multiple device terminals 332 for connecting and communicating with information system server 330. Device terminals 332 may include personal computers, personal data assistances, mobile devices such as laptops, tablet computers, augmented reality devices, or smartphones, configured with software for communications with information system server 330 via network 310.

Patient care device 312 includes a system for providing patient care, such as that described in Eggers et al., which is incorporated herein by reference for that purpose. Patient care device 312 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 312 comprises a control module 314, also referred to as interface unit 314, connected to one or more functional modules 316, 318, 320, 322. Interface unit 314 includes a central processing unit (CPU) 350 connected to a memory, for example, random access memory (RAM) 358, and one or more interface devices such as user interface device 354, a coded data input device 360, a network connection 352, and an auxiliary interface 362 for communicating with additional modules or devices. Interface unit 314 also, although not necessarily, includes a main non-volatile storage unit 356, such as a hard disk drive or non-volatile flash memory, for storing software and data and one or more internal buses 364 for interconnecting the aforementioned elements.

In various implementations, user interface device 354 is a touch screen for displaying information to a user and allowing a user to input information by touching defined areas of the screen. Additionally or in the alternative, user interface device 354 could include any means for displaying and inputting information, such as a monitor, a printer, a keyboard, softkeys, a mouse, a track ball and/or a light pen. Data input device 360 may be a bar code reader capable of scanning and interpreting data printed in bar coded format. Additionally or in the alternative, data input device 360 can be any device for entering coded data into a computer, such as a device(s) for reading a magnetic strips, radio-frequency identification (RFID) devices whereby digital data encoded in RFID tags or smart labels (defined below) are captured by the reader 360 via radio waves, PCMCIA smart cards, radio frequency cards, memory sticks, CDs, DVDs, or any other analog or digital storage media. Other examples of data input device 360 include a voice activation or recognition device or a portable personal data assistant (PDA). Depending upon the types of interface devices used, user interface device 354 and data input device 360 may be the same device. Although data input device 360 is shown in FIG. 3 to be disposed within interface unit 314, it is recognized that data input device 360 may be integral within a pharmacy system or located externally and communicating with pharmacy system through an RS-232 serial interface or any other appropriate communication means. Auxiliary interface 362 may be an RS-232 communications interface, however any other means for communicating with a peripheral device such as a printer, patient monitor, infusion pump or other medical device may be used without departing from the subject technology. Additionally, data input device 360 may be a separate functional module, such as modules 316, 318, 320 and 322, and configured to communicate with controller 314, or any other system on the network, using suitable programming and communication protocols.

Network connection 352 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 316, 318, 320, 322 are any devices for providing care to a patient or for monitoring patient condition. As shown in FIG. 3, at least one of functional modules 316, 318, 320, 322 may be an infusion pump module such as an intravenous infusion pump for delivering medication or other fluid to a patient. For the purposes of this discussion, functional module 316 is an infusion pump module. Each of functional modules 318, 320, 322 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor or an intracranial pressure monitor or the like. Functional module 318, 320 and/or 322 may be a printer, scanner, bar code reader or any other peripheral input, output or input/output device.

Each functional module 316, 318, 320, 322 communicates directly or indirectly with interface unit 314, with interface unit 314 providing overall monitoring and control of device 312. Functional modules 316, 318, 320, 322 may be connected physically and electronically in serial fashion to one or both ends of interface unit 314 as shown in FIG. 3, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 314. As described above, additional medical devices or peripheral devices may be connected to patient care device 312 through one or more auxiliary interfaces 362.

Each functional module 316, 318, 320, 322 may include module-specific components 376, a microprocessor 370, a volatile memory 372 and a nonvolatile memory 374 for storing information. It should be noted that while four functional modules are shown in FIG. 3, any number of devices may be connected directly or indirectly to central controller 314. The number and type of functional modules described herein are intended to be illustrative, and in no way limit the scope of the subject technology. Module-specific components 376 include any components necessary for operation of a particular module, such as a pumping mechanism for infusion pump module 316.

While each functional module may be capable of a least some level of independent operation, interface unit 314 monitors and controls overall operation of device 312. For example, as will be described in more detail below, interface unit 314 provides programming instructions to the functional modules 316, 318, 320, 322 and monitors the status of each module.

Patient care device 312 is capable of operating in several different modes, or personalities, with each personality defined by a configuration database. The configuration database may be a database 356 internal to patient care device, or an external database 337. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 312 location in the hospital or hospital computer network. Patient care information may be entered through interface device 354, or the data input device 360, or auxiliary interface 362, and may originate from anywhere in network 310, such as, for example, from a pharmacy server, admissions server, laboratory server, and the like.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 312 and network 310 may communicate via automated interaction, manual interaction or a combination of both automated and manual interaction. Automated interaction may be continuous or intermittent and may occur through direct network connection 352 (as shown in FIG. 3), or through RS232 links, MIB systems, RF links such as BLUETOOTH, IR links, WLANS, digital cable systems, telephone modems or other wired or wireless communication means. Manual interaction between patient care device 312 and network 310 involves physically transferring, intermittently or periodically, data between systems using, for example, user interface device 354, coded data input device 360, bar codes, computer disks, portable data assistants, memory cards, or any other media for storing data. The communication means in various aspects is bidirectional with access to data from as many points of the distributed data sources as possible. Decision-making can occur at a variety of places within network 310. For example, and not by way of limitation, decisions can be made in a remote data server, a hospital department or unit stations, or within patient care device 312 itself.

All direct communications with medical devices operating on a network in accordance with the subject technology may be performed through information system server 330, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

Figure 4A:
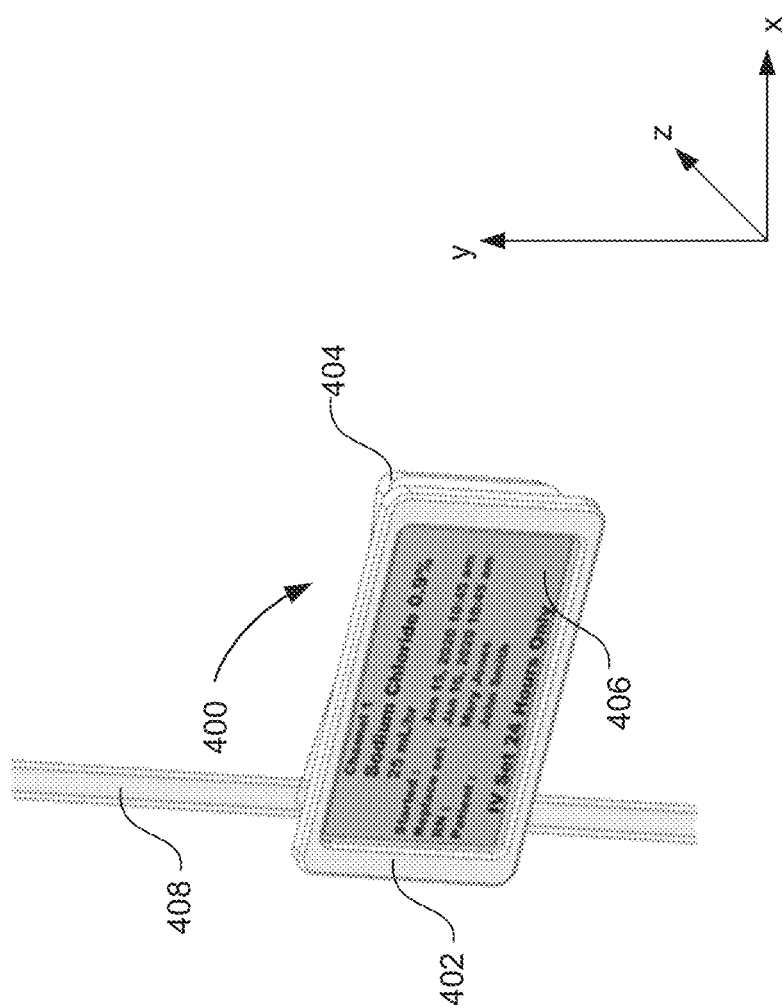
FIGS. 4A-4G depict various views of an electronic tag, according to aspects of the subject technology.

FIG. 4A shows an electronic tag 400 that is configured with a display screen to display pertinent information relevant to an infusion process, according to aspects of the subject technology. The electronic tag 400 is configured to visually associate an IV administration set (or fluid line) to a particular infusion container and/or a particular infusion device. The infusion container may be, for example, the IV bag 38 shown in FIG. 1. The IV bag 38 includes a fluid that is infused, using an IV set 408 connecting the IV bag 38 and the infusion pump 22, to a patient. The administration set may, in some implementations, provide a gas from a source such as a tank to a patient through a device configured to regulate the flow of gas such as a ventilator. The electronic tag 400 may provide similar association features for a line including gas as described for fluids.

The electronic tag 400 includes a front portion having a housing 402. In some implementations, the housing 402 encloses one or more of a processor, memory, power storage, an antenna, sensors, and a data communication component. In some implementations, the data communication component is a transceiver that is coupled to the processor. In some implementations, the transceiver is a Bluetooth transceiver. In some implementations, the transceiver is a RFID transceiver. In some implementations, a display 406 is coupled to the processor and is configured to display information received via the transceiver. In some implementations, the display 406 is an electronic ink display. The electronic ink display may display different colors, and the color may be used to identify the different IV lines.

Alternatively or additionally, the electronic tag 400 may include additional colored LED components to indicate if a fault has been detected for an infusion process. For example, the electronic tag 400 may include colored or color-adjustable LED that allows a general status indication of the infusion process to be visible even from a distance. The LED may be mounted within, upon, or externally on the housing of the electronic tag 400. A clinician can see the green LED, if lit, from a distance and be informed that that the infusion process is proceeding normally. In some implementations, the electronic tag 400 may include a red or yellow LED. Likewise, the clinician can see the red or yellow LED, when lit, from a distance and be informed that the infusion process may need some troubleshooting. In some implementations, the color of the LED may be coded to provide additional information to the clinician about the status of the infusion process. Additionally or in the alternative, these colored LED components may be represented by corresponding colored graphic indicators (e.g., a group of pixels in the form of an LED) presented by display 406.

The electronic tag 400 also includes communication components and/or antenna that allow the electronic tag 400 to be programmed, in some implementation, by wireless technology (e.g., Bluetooth, Wi-Fi, near-field communication (NFC)). In some implementations, the electronic tag 400 may communicate with the infusion pump (e.g., using the data communication component, and/or the antenna) to coordinate with alarm systems at the pump or at a nursing station. For example, the electronic tag 400 may receive information from the pump that at the infusion container is empty, and generate an alert that the infusion container is empty, prior to the infusion line emptying and drawing air into the system. For example, a sensor may be included in the electronic tag to provide information about a fluidic pressure in the IV line. In some implementations, the infusion pump includes software to convert signals sent by the electronic tag 400 into actionable messages to a clinician (e.g., change the infusion container).

In some implementations, the electronic tag 400 may also communicate with a medication safety and continuous quality improvement (CQI) software at the point of care. The point of care may include the programming module 60 and/or the infusion pumps. The software, when deployed at the programming module 60 and/or the infusion pumps, may help reduce IV medication errors, improve the overall quality of patient care, track and measure system performance and help increase compliance with national safety standards. In some implementations, the software allows for customizable care areas or profiles. Within each of these profiles, drug and IV fluid libraries may be created. The names of the drugs and IV fluids may be customized with generic or brand name medications and help distinguish look-a-like names. The software may also create drug-specific clinical advisories that provide additional clinical information prior to the start of the infusion. The software may also allow drug-specific therapies to customize patient-specific infusion delivery limits. For example, once the electronic flip 400 is associated with a particular IV container holding a particular medical fluid, the electronic tag 400 may communicate the identity of the medical fluid to the pump, which then determine a range of infusion rates for that the medical fluid from a drug library containing information about various medical fluids. The clinician is then able to select, on the programming module 60 and/or the infusion pump, an infusion rate from within the range of infusion rates, and the electronic tag 400 may then display the selected infusion rate. The electronic tag 400 is configured to receive from the infusion pump, through the transceiver, infusion information obtained via the software about a content of the IV infusion container, and infusion parameters of an infusion process associated with the IV infusion container.

In some implementations, the electronic tag 400 does not include communication components, and the electronic tag is configured to be used alone, for example, in a gravity infusion, without the infusion pump. In some implementations, the electronic tag configured for use with gravity infusion may include Bluetooth functionalities that provide communication and location signals to a network of the hospital system. The system may then detect and determine where in the hospital the gravity infusion is occurring.

A back portion of the electronic tag 400 includes a clamping mechanism 404. The clamping mechanism 404 is configured to secure the electronic tag 400 to an IV tubing of the IV set 408. The clamping mechanism 404 includes a first elongated receptacle 414, formed on a back portion 413 of the housing 402 to receive the IV tubing of the IV set 408. Together with a second elongated receptacle 412, the receptacles 412 and 414 are shaped to snugly restrain a portion of the tubing of the IV set 408 without occluding a flow of the fluid in the tubing. The receptacles 412 and 414 jointly surround the portion of the tubing of the IV set 408. In some implementations, as shown in FIG. 4B and FIG. 4C, the receptacles 412 and 414 are V-shaped grooves that jointly enclose a length of the tubing between the clamp arm 416 and the first elongated receptacle 414.

Figure 4B:
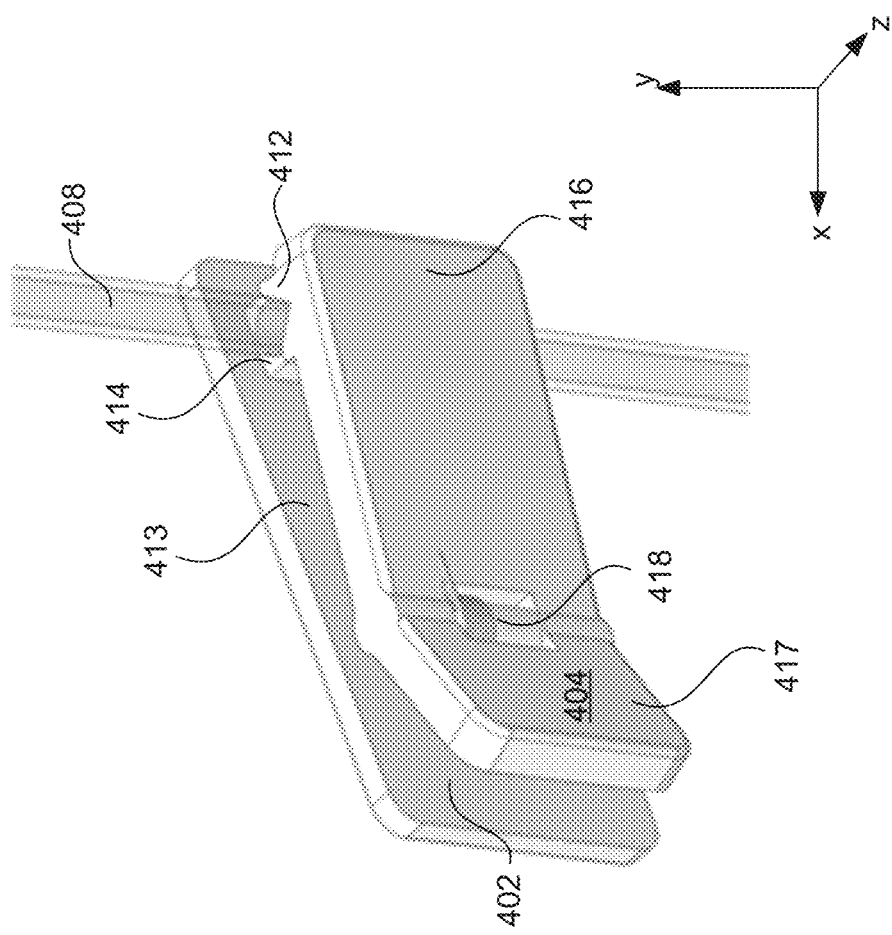

FIG. 4B shows a back view of the electronic tag 400. The electronic tag 400 includes the clamping mechanism 404 having a clamp arm 416. In general, the electronic tag 400 can be securely attached using any mechanism that does not occlude a flow of fluid in the tubing. In some implementations, as shown in FIG. 4B, the clamping mechanism 404 includes a swivel joint and spring 418 (e.g., pivotably coupling housing 402 and arm 416) that exerts a mechanical force (e.g., applies tension to the clamp arm 416) on the second receptacle 412 when no external force is applied to a lever 417 of the clamping mechanism 404.

The electronic tag 400 may be easily attached to a tubing of the IV set by applying force to lever 417 to move clamp arm 416 away from housing 402 and open receptacles 412 and 414 to receive the tubing, before releasing the force on lever 417. In some implementations, the electronic tag 400 may incorporate additional components to ensure that the electronic tag 400 is locked in place during an infusion process and is only removed by authorized person(s). For example, the electronic tag 400 may be locked by an electromechnical device. For example, the electromechanical device receives a wireless control signal from the infusion pump to unlock the electronic tag 400 when the infusion pump detects an authorized person at the electronic tag 400 at the end of an infusion process, or when the IV container and/or the IV set is being replaced. In some implementations, the electronic tag 400 can also be "locked" to the tubing by virtue of a proximity sensor. For example, the clamping mechanism 404 may have a magnet in it and the electronic tag 400 may have a Hall effect sensor which registers that the clamping mechanism 404 is in a "closed" state. Once the electronic tag 400 is associated to the infusion pump (e.g., infusion pump 22) the electronic tag 400 can sense whether the "clamp closed" signal has been interrupted and post an error message when the "clamp closed" signal has been interrupted. Similarly, the electronic tag 400 may include other communication functionalities, for example, the electronic tag 400 may provide location information of the electronic tag to the pump and/or transmit other information to the pump.

Figure 4C:
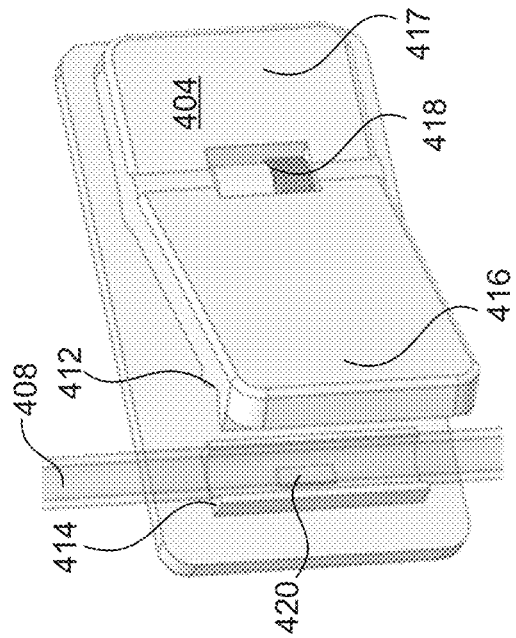

FIG. 4C shows a back view of the clamping mechanism 404 when an external force is applied to the lever 417, according to aspects of the subject technology. For example, when a clinician presses down on the lever 417 so that the lever 417 is substantially parallel to a plane of the housing 402, the first receptacle 414 is separated from the second receptacle 412. As shown in FIG. 4C, a sensor 420 is positioned within the receptacle 414. In some implementations, the sensor 420 is a pressure sensor that is configured to measure a fluidic pressure of the fluid in the tubing of the IV set 408 at the location of the sensor 420. In some implementations, the pressure sensor is an electronic flow sensor that uses a data communication component disposed within the housing 402 to transmit measured data to the infusion pump.

In some implementations, when the IV container is squeezed, the sensor 420 detects an increase in pressure and helps to identity if the electronic tag 400 is attached to the correct tubing. The sensor 420 may also be used to detect when the IV container is empty.

In some implementations, the sensor 420 includes an acoustic sensor. The acoustic sensor may detect acoustic waves, sounds or noises within the fluid line as the infusion fluid is flowing past the sensor. The detected noise may be used to identify the flow rate. In some implementations, the acoustic sensor includes an ultrasonic method of flow sensing.

In some implementations, the electronic tag 400 works in conjunction with an acoustic transducer that generates an acoustic wave that is detected by the sensor 420 in the electronic tag 400. In such cases, instead of a clinician physically squeezing the IV container to match a particular IV set to an IV container, an acoustic transducer can be attached to a particular IV container. The acoustic sensor in the electronic tag 400 (attached to the IV set) determines if it detects an acoustic signal generated by the acoustic transducer attached to the IV container to check if the electronic tag 400 is correctly associated with that particular IV container. In some implementations, the electronic tag 400 may further include an emitter (e.g., an acoustic transducer or a pressure actuator) that generates acoustic signals or pressure signals to allow association between the IV administration line and the infusion pump (and/or a second electronic tag).

In some implementations, the acoustic signal may be generated by the infusion pump. For example, the infusion pump may move its motor(s) back and forth to generate a signature acoustic pattern that is transmitted through the IV set to the electronic tag 400.

The signal (e.g., acoustic signal, pressure signal) emissions and detections performed by acoustic transducers or pressure actuators and sensors in the electronic tags may be coordinated as follows:

The process may begin with the electronic tag 400 receiving an indication that it is time to check the IV administration lines (e.g., "line tracing"). The indication may be provided by an element paired with the electronic tag 400. For example, the element paired with the electronic tag 400 may be a second electronic tag, the infusion pump 22, or the programming module 60.

The clinician may first determine that the electronic tag 400 is affixed to an IV administration line (e.g., based on the position where the clamping mechanism 404 of the electronic tag 400 attaches the electronic tag to the IV administration line).

The electronic tag 400 may transmit a "ready to emit" initiation signal, and the pair element may optionally provide a received signal acknowledgment. The initiation signal may cause adjustment of a detection device, for example, in the other electronic tags, infusion pump 22, or programming module 60. The adjustment may include activating the detection device or adjusting a detection threshold for a period of time.

The acoustic transducer or pressure actuator in the electronic tag 400 causes one or more emissions of either acoustic waves or pressure waves. The electronic tag 400 and/or the paired element receives an acknowledgement that the line tracing is successful. In some implementations, the acknowledgement may be received directly through interactions with the electronic tag. In some implementation, the acknowledgement is received through a signal from the infusion pump 22, the programming module 60, or interaction with other components in the infusion process.

In some implementations, an acoustic transducer in the electronic tag may transmit an acoustic signal to the infusion pump so that the infusion pump can verify that the correct electronic tag 400 is associated to the infusion pump. The infusion pump may detect if a signature acoustic pattern was transmitted from a particular electronic tag along an IV set. In such a manner, various associations may be carried out: (1) from the IV container to the electronic tag, and (2) from the electronic tag to the infusion pump. In some implementations, additional electronic tags may be used to correctly associate the IV set from the pump to the patient, as described in more details below.

In some implementations, the patient may be provided with a device that receives communication signals from the infusion pump and/or the electronic tag. For example, the device may be a wrist band that allows the pump to communicate information from the electronic tag 400 to the patient, or for the electronic tag 400 to directly communicate information to the patient.

Figure 4E:
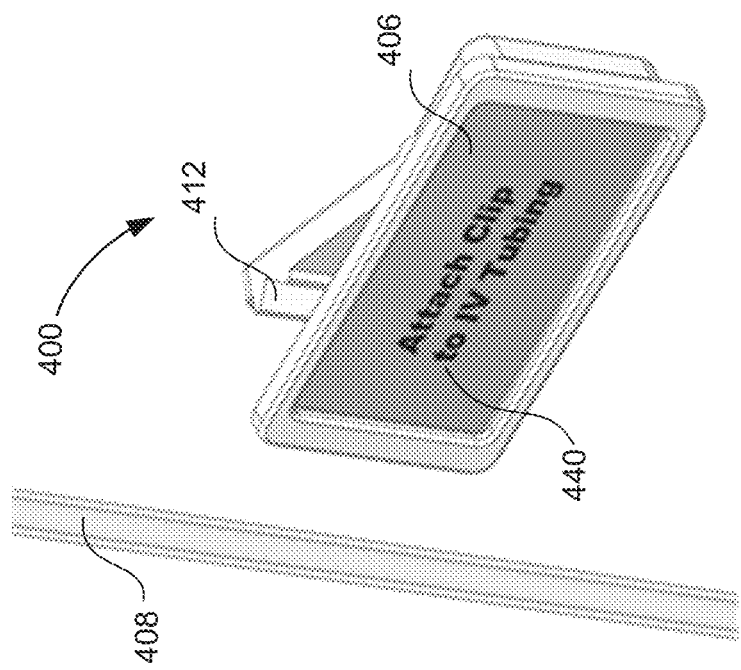
Figure 4D:
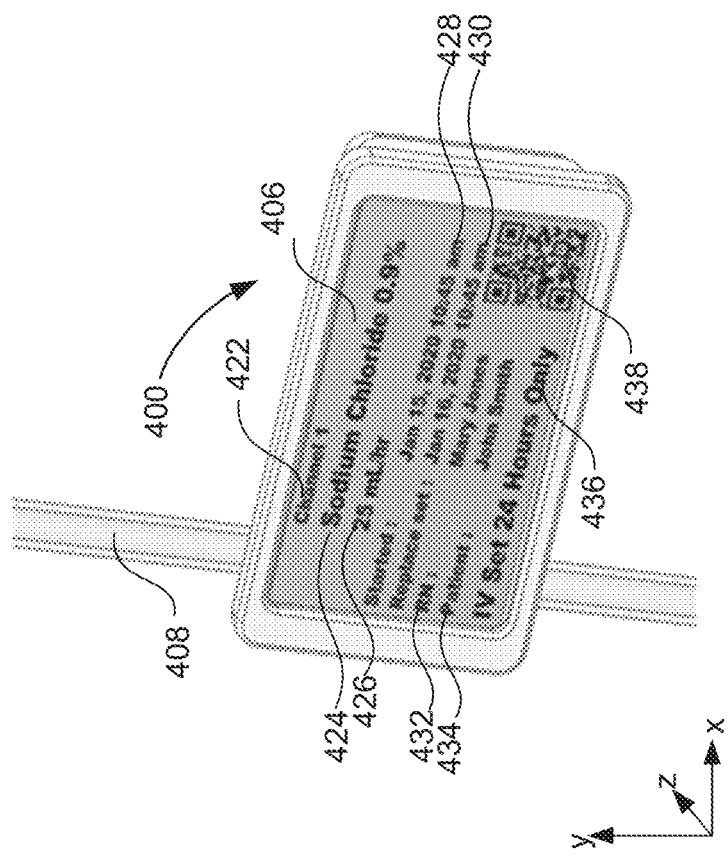

FIG. 4D shows a close-up view of the display 406 of the electronic tag 400. In some implementations, the electronic tag 400 is a stand-alone device that allows the display 406 to present legible information to the clinician and/or patient without the need for any additional accessories. For example, the electronic tag 400 may be self-powered, and no power cords are needed to power the electronic tag during use. In some implementations, the electronic tag 400 includes a rechargeable battery that has sufficient electrical (e.g., charge) storage capacity to power the electronic tag 400 for the duration of an infusion, and/or until the use period of the IV administration set has expired (e.g., up to 96 hours). In some implementations, the electronic tag 400 is reusable, and data containing pertinent information about each infusion process is transmitted to the electronic tag 400 prior to the start of every infusion process.

The electronic tag 400 provides sufficient power so that the display 406 is able to present information about an infusion process over the intended usage period of an IV set. In some implementations, the IV set can be used for up to 96 hours. In some implementations, the IV set can be used for up to 72 hours. For safety reasons, IV sets are replaced once they have been used for their intended usage duration to ensure that the IV sets maintain their specified performance characteristics.

The electronic tag 400 is a low cost element that may enhance the safety and accuracy of the infusion process. The display 406 may be used to show information pertinent to an infusion process, allowing the electronic tag 400 to be a smart tag that provides updated and accurate information to a clinician and/or patient.

The electronic tag 400 may also permit an infusion process to be set up and carried out with less manual labor while increasing the accuracy and safety of the infusion process. A clinician may rely on the intelligent tag to help her in accurately associating the IV container to a particular IV set and a particular infusion pump. For example, the display 406 shows: (i) channel information 422 about the infusion pump the IV set 408 is connected to; (ii) information 424 about the medical fluid contained in the IV container that is being infused; (iii) information 426 about the infusion rate of the medical fluid; (iv) information 428 about a starting time of the infusion; (iv) the time the IV set's usage would exceed the intended usage period is shown in the display 406 as information 430; (v) information 432 about the clinician who started the infusion process; and (vi) information 434 about the patient who is receiving the infusion.

In some implementations, information 436 is provided in larger font size on the display 406 to notify the clinician and/or the patient about the intended usage period of the IV set. In some implementations, the display 406 further shows a countdown timer to the time the IV set 408 needs to be replaced. In this way, the electronic tag 400 provides more functionalities than just a tag or a display. The electronic tag 400 may also provide timely warning or error messages so that a clinician can promptly correct any fault status associated with the infusion process.

A machine-readable code (e.g., a linear barcode, a 2D barcode, a quick read code) 438 may be used, in some implementations, for tracking and recording steps of the infusion process, such as tracking the medication prescribed to a specific patient and/or for other purposes.

Figure 4G:
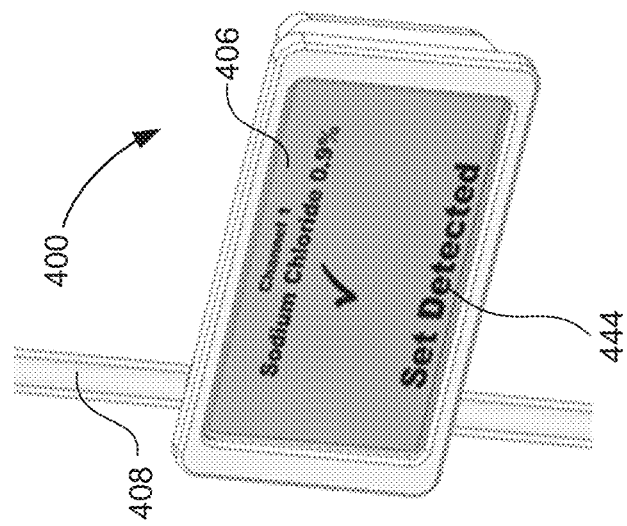
Figure 4F:
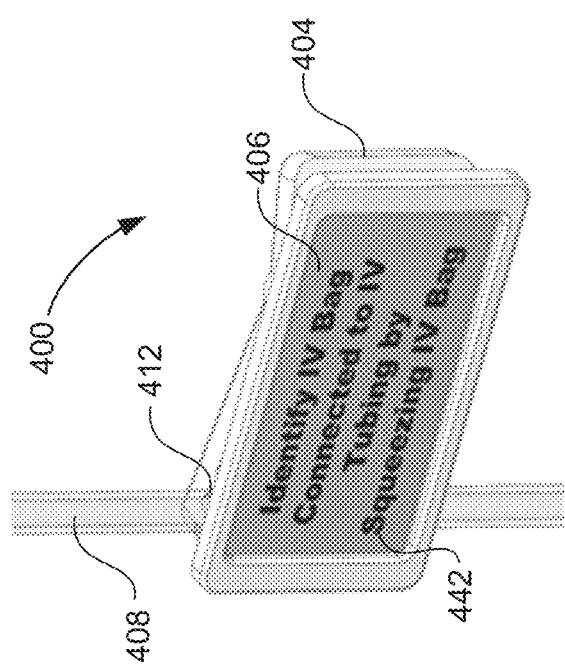

FIGS. 4E-4G illustrate how the electronic tag 400 is associated with a particular IV set used to deliver infusion fluid from an IV container to a patient, according to aspects of the subject technology. In some implementation, when the electronic tag 400 is first activated for use, an introductory message 440 is shown on the display 406. For example, the electronic tag 400 may be activated for use for the first time when the lever 417 of the clamping mechanism 404 is depressed so that the lever 417 is substantially parallel to a plane of the housing 402 (for example, as shown in FIG. 4C). In some implementations, the introductory message 440 may provide step-by-step instructions to the clinician to correctly associate the IV set to an IV container. For example, in some implementations, the introductory message 440 provides the first instruction for the clinician to attach the electronic tag 400 to the IV tubing.

FIG. 4F shows a subsequent step in the process for correctly associating the IV set with an IV container, according to aspects of the subject technology. In some implementations, once the sensor 420 on the electronic tag 400 senses that the electronic tag 400 has been attached to a tubing of the IV set 408, the display 406 provides an updated message 442 containing a subsequent instruction for associating the electronic tag 400 with a particular IV container.

For example, the message 442 directs the clinician to squeeze the IV container (e.g., IV bag) which contains the medical fluid the clinician wishes to infuse to a patient using the IV set to which the electronic tag 400 has been attached. When the clinician squeezes the IV container, there is a change in the fluidic pressure detected at the sensor 420 disposed within the first elongated receptacle 414 on the back portion of the housing 402 (caused by the squeeze). The processor disposed in the housing 402 of the electronic tag is able to analyze the signal received from the sensor 420 to confirm that the IV bag squeezed by the clinician is correctly associated with the IV set 408.

Conversely, when the sensor 420 expects an increase in fluidic pressure but no such pressure variation is detected, the electronic tag 400 may display a warning message that it has not yet been correctly associated with an IV container. The electronic tag 400 may also transmit, via Bluetooth, a warning message to the pump, and/or to a nursing station, notifying the clinician that the IV set has not been properly associated with the IV container.

In some implementations, the message 442 may further direct the clinician to provide a sequence of squeezes so that a pattern of pressure variation is detected at the sensor 420 to provide a more accurate association between the IV container that is squeezed and the IV set 408 to which the electronic tag 400 is attached (e.g., by eliminating spurious noise that might give rise to a "false-positive" association between the IV container and the IV set 408).

In some implementations, an acoustic transducer is placed near or on the IV container, and is activated to send a series of acoustic waves into the medical fluid that is detected by the sensor 420. In some implementations, a data communication component disposed within the housing 402 of the electronic tag may communicate directly with the acoustic transducer placed at or near the IV container and sends a request for the acoustic transducer to generate a series of acoustic pulses. In some implementations, the series of acoustic pulses is modulated.

In some implementations, the series of modulated acoustic pulses is detected by the sensor 420, and the detected signal is analyzed by the processor disposed within the housing 402 to ensure that the modulated acoustic pulses match the series of acoustic pulses that was emitted by the acoustic transducer. In some implementations, the signal detected by the sensor 420 is communicated wirelessly to the infusion pump, and the infusion pump then sends a control signal to the electronic tag 400 to display a completion message 444 when the pump determines that the modulated acoustic signal detected by the sensor 420 matches signal generated by the acoustic transducer placed at or near the IV container. When the detected modulated acoustic pulses deviate from the expect modulated acoustic pulses by an amount greater than a threshold, the electronic tag 400 may also transmit, for example, via Bluetooth, a warning message to the infusion pump, and/or to a nursing station, notifying the clinician that the IV set has not been properly associated with an IV container.

When the sensor 420 successfully detects a variation in fluidic pressure or a modulated acoustic signal, the electronic tag 400 may then present a completion message 444 on the display 406, informing the clinician that the IV set has been detected and confirmed to be correctly associated with the IV container. The identity of the medical fluid in the IV container is also presented on the display 406, as an additional check that the IV container has been correctly associated. The name of the infusion pump (e.g., "Channel 1") may also be shown on the display 406 to ensure that the IV set 408 is correctly connected to the desired infusion pump.

In some implementations, the electronic tag 400 is associated with the IV container and/or infusion pump through a near-field communication (NFC) component within the electronic tag 400. The NFC component allows one-to-one associations between the IV container and/or infusion pump when the electronic tag 400 establishes a wireless communication. In some implementations, after the clinician scans a code (e.g., machine-readable code 438 in FIG. 4D) of the electronic tag 400, the programming module 60 selects an infusion pump to be the active infusion pump and the IV set can be loaded to connect with that specific infusion pump.

In some implementations, two or more electronic tags may be used in conjunction for a particular IV set. For example, a first electronic tag of a pair of electronic tags may be attached to the IV container, and the second electronic tag may be attached on the IV set, upstream of the pump. When both tags are placed on the fluid path between the IV container and the pump, information may be sent to the electronic tag in different ways.

In some implementations, the pump already has information about the IV container through methods other than display of information provided by the electronic tags (e.g., from scanning of barcodes, or other ways of associating the IV container to the pump). The pump then transmits that information to the electronic tags via RFID or Bluetooth. In some implementations, acoustic signal exchanges between the electronic tags are initiated to verify that the correct devices are receiving the wireless information.

In some implementations, the IV container includes an RFID or Bluetooth transmitter tag affixed on it that allows the IV electronic tag to receive information directly from the IV container. Information encoded in the RFID or Bluetooth transmitter tag disposed the IV container may have been preloaded at the pharmacy. In some implementations, acoustic signal exchanges between the electronic tags are initiated to verify that the correct devices are receiving the wireless information.

Alternatively, the first electronic tag of the pair may be attached at a first location on the IV set, upstream of the pump. The second electronic tag may be attached at a second location on the IV set, downstream of the pump (e.g., between the pump and the patient). In some implementations, the electronic tags communicate by acoustic signaling.

In some implementations, three electronic tags can be used in conjunction and be associated to a single pump. For example, the first tag may be associated to a primary infusion IV container, the second electronic tag may be associated to a secondary infusion IV container, and the third electronic tag is located on an IV set that makes a downstream connection from the pump to the patient.

Each electronic tag is able to generate its own acoustic signals and detect acoustic signals generated by the other electronic tag. In some implementations, the acoustic signals are propagated and detected through the medical fluid in the IV set. For example, when the acoustic signal generated by the first electronic tag at the first location of the IV set is detected by the sensor of the second electronic tag at the second location of the IV set, the pair of electronic tags is able to determine that they are correctly attached to the same infusion IV set. Similarly, a first electronic tag attached to an IV container can be correctly associated with a second electronic tag located on the IV set when the pair of electronic tags are able to detect acoustic signals generated by each other. In some implementations, an acoustic signal is detected upstream of the pump, by the pump, and then the pump generates a retransmitted acoustic signal at the downstream side in order to associate upstream and downstream tags with each other.

Figure 5A:
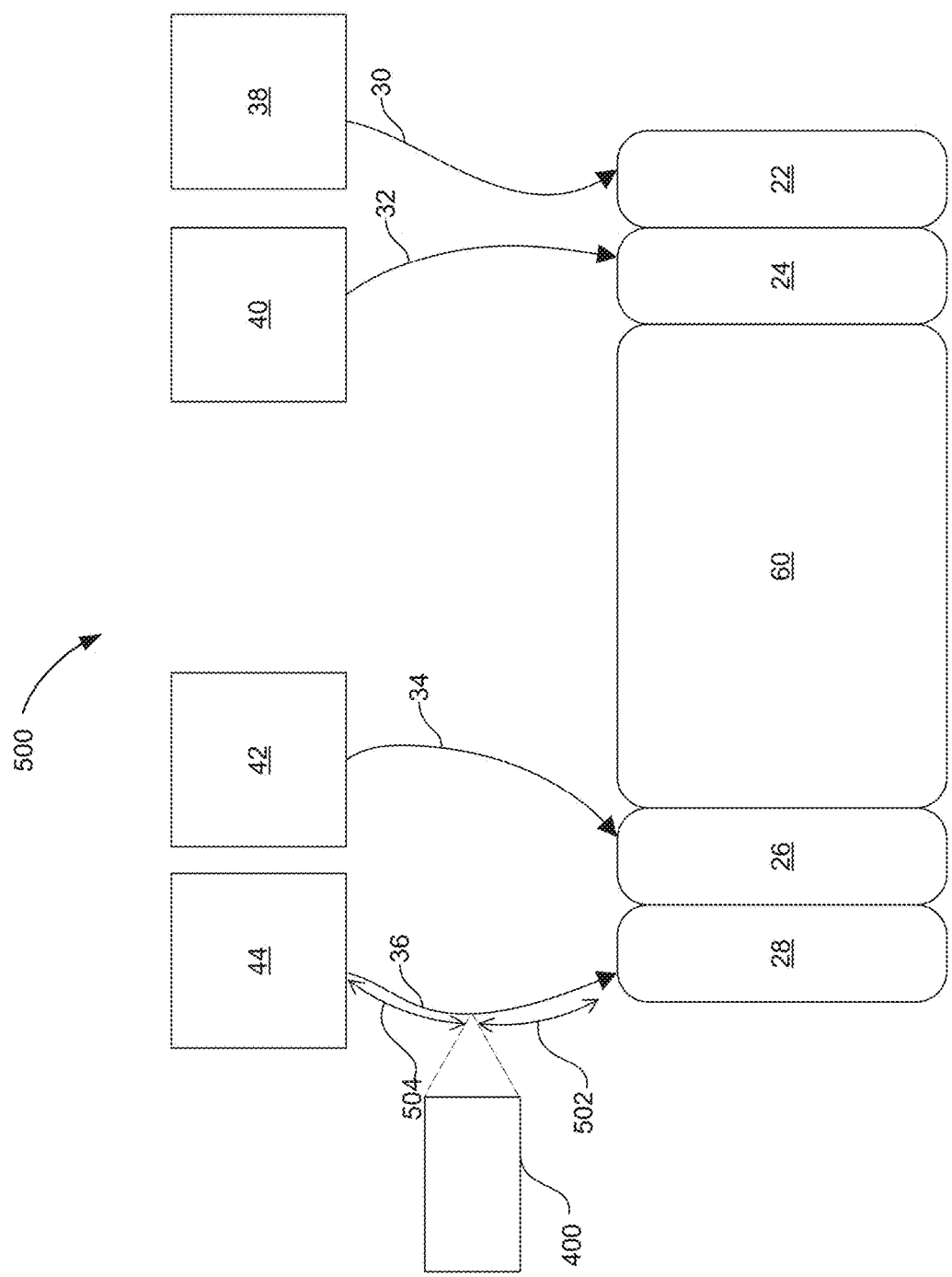
FIG. 5A is a conceptual diagram illustrating the use of the electronic tag described in FIGS. 4A-4G, according to aspects of the subject technology.

FIG. 5A shows a system 500 in which the electronic tag 400 is incorporated into the medical administration system 20 shown in FIG. 1. The four fluid containers 38, 40, 42, and 44 are connected to infusion pumps 22, 24, 28, and 26 respectively, and the infusion pumps 22, 24, 26, and 28 are all attached to the programming module 60. The electronic tag 400 is attached on IV set 36. There may be additional electronic tags attached to respective IV sets that are not illustrated in FIG. 5A. In some implementations, the electronic tag 400 is able to communicate upstream 504 and downstream 502 of the electronic tag 400. For example, the electronic tag 400 is able to receive acoustic signals generated upstream of the clip and to transmit acoustic signals downstream of the electronic tag 400 to the infusion pump 28. The acoustic signals may be modulated, allowing an acoustic sensor receiving the acoustic signal to ascertain the source of the acoustic signal.

FIG. 5B shows the system 500 in which the electronic tags 506, 508, 510 and 512 are attached to the IV sets 36, 34, 32, and 30, respectively. The IV set 30 has been partially swapped with the IV set 32, causing the IV set 30 to associate the fluid container 38 with the infusion 24. When the clinician is unaware that the IV set 30 has been erroneously swapped with the IV set 32, the electronic clip 512 may, in some implementations, generate a warning on its display or cause the infusion pump 22 to generate an alarm. For example, the infusion pump 24 may have been pre-programmed to receive the medical fluid in fluid container 40 and to infuse the medical fluid to a patient 518 at a specific infusion rate. Instead, the infusion pump 24 receives fluid from the fluid container 38 and may then infuse the fluid from the fluid container 38 at the wrong set infusion rate to the patient. To reduce the likelihood of such a line swap, an acoustic transducer housed within the electronic tag 510 may generate an acoustic signal that is intended for a sensor associated with the infusion pump 24, which may be situated proximate to the infusion line. When the sensor associated with the infusion pump 24 fails to receive the signal generated by the acoustic transduced from electronic tag 510, the pump may display or sound an alert or may wirelessly deliver a warning message to the electronic tag 510 for presentation on a display of the electronic tag 510. Lines 514 and 516 are schematic illustrations showing the output of the various infusion pumps 22, 24, 26, and 28 being delivered to the patient 518. In some implementations, the line 514 includes a central line. A central line includes a catheter that is placed into a large vein. In some implementations, the line 516 includes an antecubital line. An antecubital line may be inserted into a vein in the patient's arm. The patient 518 may be equipped with a smart wrist band that transmits information from the electronic tag to the patient. For example, the information presented on the display 406 may be additionally provided to a display on the smart wrist band. The display on the smart wrist band may be an electronic paper display technology such those commercially available from E Ink Corporation. The patient is then able to receive information about the identity of the medical fluid that is being infused, and also receive information about when the IV set would have to be replaced.

Many of the above-described devices, systems and methods, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

In some implementations, an electronic tag includes a housing; a processor within the housing; a transceiver configured within the housing and coupled to the processor; a display coupled to the housing and the processor, and configured to display information received via the transceiver; a clamping mechanism coupled to the housing and configured to secure the electronic tag to an intravenous (IV) tubing; and a sensor configured within the housing, and configured to measure a property of a fluid in an IV tubing at a location of the clamping mechanism.

In some implementations, the processor is configured to send, via the transceiver, first signals to an infusion device and to receive, via the transceiver, second signals from the infusion device. In some implementations, the first signals sent to the infusion device is configured to trigger an alarm at a location remote to the electronic tag when a fault condition exists. In some implementations, the transceiver comprises a wireless communication device and is configured to communicate with the infusion device via a wireless connection. In some implementations, the processor is configured to cause the electronic tag to receive from the infusion device, through the transceiver, infusion information about a content of the IV infusion container, and infusion parameters of an infusion process associated with the IV infusion container; and the display is configured to display the infusion information and the infusion parameters.

In some implementations, the housing includes a first elongated receptacle configured to receive a portion of the IV tubing, and the clamping mechanism includes a clamp arm and a spring configured to apply tension to the clamp arm to restrain the portion of the IV tubing within the first elongated receptacle. In some implementations, the display is disposed on a first side of the housing, opposite the first elongated receptacle and the clamp arm. The clamp arm includes a second elongated receptacle, the first elongated receptacle and the second elongated receptacle being configured to jointly surround the portion of the IV tubing to restrain at least the portion of the IV tubing between the clamp arm and the first elongated receptacle.

In some implementations, the first elongated receptacle and the second elongated receptacle form a substantially cylindrical shape when the claim arm is moved to restrain the IV tubing, and wherein the sensor is disposed within the first elongated receptacle and is configured to contact the restrained IV tubing. In some implementations, the sensor includes an acoustic sensor configured to measure acoustics within at least a portion of the IV tubing. In some implementations, the sensor includes a pressure sensor configured to detect a fluidic pressure of a fluid within the IV tubing at the location of the IV tubing. In some implementations, the electronic tag further includes a lock to secure the electronic tag to the IV tubing.

In some implementations, the electronic tag further includes at least one colored light emitting diode (LED). The at least one colored LED is configured to emit a first color when a fault condition exists and to emit a second color, different from the first color, during normal operation. In some implementations, the electronic tag further includes a signal emitter configured to emit signals for associating the electronic tag with an infusion device or a second electronic tag. In some implementations, the signal emitter includes an acoustic transducer or a pressure actuator.

In some implementations, a method of associating an intravenous (IV) infusion container to an infusion pump of an infusion device include receiving, at the infusion pump, an IV tubing coupled with the IV infusion container. An electronic tag is affixed to the IV tubing, and the electronic tag includes a housing; a processor within the housing; a transceiver configured within the housing and coupled to the processor; a display coupled to the housing and the processor, and configured to display information received via the transceiver; a clamping mechanism coupled to the housing and configured to secure the electronic tag to an intravenous (IV) tubing; and a sensor configured within the housing, and configured to measure a property of a fluid in an IV tubing at a location of the clamping mechanism. The method includes causing a signal to be transmitted from at least one of the IV infusion container and the infusion pump of the infusion device. The method includes receiving, from the electronic tag, a confirmation message indicating that the sensor of the electronic tag received an association signal. The method includes determining that the association signal corresponds to the signal transmitted by the at least one of the IV infusion container and the infusion pump. The method includes causing the electronic tag to display a message on the display of the electronic tag indicating an association with the IV infusion container or the infusion pump of the infusion device.

In some implementations, causing the signal to be transmitted from the IV infusion container includes applying a pressure to the IV infusion container. The sensor of the electronic tag includes a pressure sensor, and the confirmation message indicates that the electronic tag detected an increase in a fluidic pressure in the IV tubing caused by the pressure applied to the IV infusion container. In some implementations, the method further includes causing the display of the electronic tag to display an instruction for applying the pressure to the IV infusion container. Displaying of the message is based at least in part on determining that the confirmation message is received within a first time period measured from a time the instruction was displayed. In some implementations, transmitting the signal at the infusion pump of the infusion device includes transmitting an acoustic signal within the IV tubing at the infusion pump of the infusion device; and the sensor of the electronic tag includes an acoustic sensor. The confirmation message indicates that the electronic tag measures a detected acoustic signal in the IV tubing caused by the acoustic signal generated at the infusion pump of the infusion device.

In some implementations, the acoustic signal generated at the infusion pump of the infusion device comprises a modulated acoustic signal, the modulated acoustic signal is caused by variations in movements of a pump in the infusion device. The confirmation message indicates a detected modulation of the detected acoustic signal in the IV tubing corresponds to a modulation of the modulated acoustic signal generated at the infusion pump of the infusion device.

In some implementations, causing the electronic tag to display the message is based at least in part on determining that the confirmation message is received within a threshold period of time measured from a time of the transmission of the signal.

In some implementations, the method further includes transmitting, from the infusion device, information about a content of the IV infusion container, and parameters of an infusion process associated with the IV infusion container; and causing the electronic tag to display the information and the parameters on the display of the electronic tag.

In some implementations, a method of associating an intravenous (IV) infusion container to an infusion pump of an infusion device, the method includes determining, at an electronic tag, that the electronic tag is affixed to an IV tubing coupled with the IV infusion container. The electronic tag includes a housing; a processor within the housing; a transceiver configured within the housing and coupled to the processor; a display coupled to the housing and the processor, and configured to display information received via the transceiver; a clamping mechanism coupled to the housing and configured to secure the electronic tag to an intravenous (IV) tubing; and a sensor configured within the housing, and configured to measure a property of a fluid in an IV tubing at a location of the clamping mechanism. The method includes receiving a signal transmitted from at least one of the IV infusion container and the infusion pump of the infusion device. The method includes generating, by the electronic tag, based on the signal, a confirmation message indicating that the sensor of the electronic tag received an association signal. The method includes transmitting the confirmation message to the at least one of the IV infusion container and the infusion pump of the infusion device. The method includes receiving from the IV infusion container or the infusion pump of the infusion device a message indicating association with the IV infusion container or the infusion pump of the infusion device. The method includes causing the electronic tag to display a message on the display of the electronic tag indicating an association with the IV infusion container or the infusion pump of the infusion device.

In some implementations, a method of associating an intravenous (IV) infusion container to an infusion pump of an infusion device. The method includes attaching a first electronic tag at a first location along a fluidic path between the IV infusion container and the infusion device. The first electronic tag includes a first housing; a first processor within the first housing; a first transceiver configured within the first housing and coupled to the first processor; a first display coupled to the first housing and the first processor, and configured to display information received via the first transceiver; a first clamping mechanism coupled to the first housing and configured to secure the first electronic tag to an intravenous (IV) tubing; and a first sensor configured within the first housing, and configured to measure a property of a fluid in an IV tubing at a location of the first clamping mechanism. The method includes attaching a second electronic tag to a second location along the fluidic path, the second electronic tag includes a second housing; a second processor within the second housing; a second transceiver configured within the second housing and coupled to the second processor; a second display coupled to the second housing and the second processor, and configured to display information received via the second transceiver; a second clamping mechanism coupled to the second housing and configured to secure the second electronic tag to an intravenous (IV) tubing; and a second sensor configured within the second housing, and configured to measure a property of a fluid in an IV tubing at a location of the second clamping mechanism. The method includes generating a first signal at a first signal generator of the first electronic tag. In accordance with a determination that the second sensor of the second electronic tag receives the first signal generated at the first signal generator of the first electronic tag: displaying on the first display of the first electronic tag and displaying on the second display of the second electronic tag a message that the IV fluid infusion container is associated to the IV tubing.

Figure 6:
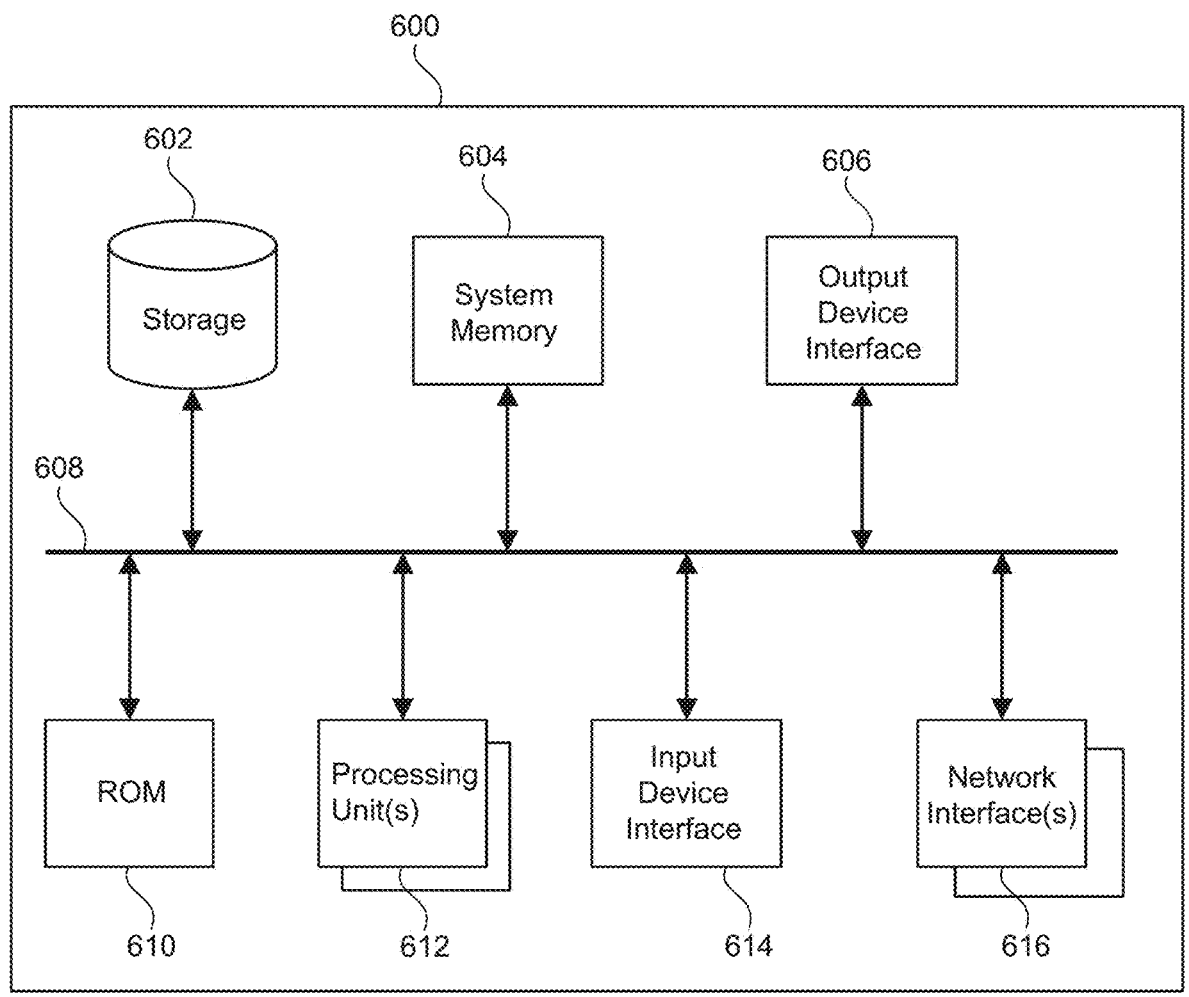
FIG. 6 is a conceptual diagram illustrating an example electronic system 600 for associating a fluid container to an infusion pump, according to aspects of the subject technology.

FIG. 6 is a conceptual diagram illustrating an example electronic system 600 for communicating with the electronic tag, according to aspects of the subject technology. Electronic system 600 may be a computing device for execution of software associated with one or more components and processes provided by FIGS. 1-5B, including but not limited to server 330, or computing hardware within patient care device 312. Electronic system 600 may be representative, in combination with the disclosure regarding FIGS. 1-5B. In this regard, electronic system 600 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 600 may include various types of computer readable media and interfaces for various other types of computer readable media. In the depicted example, electronic system 600 includes a bus 608, processing unit(s) 612, a system memory 604, a read-only memory (ROM) 610, a permanent storage device 602, an input device interface 614, an output device interface 606, and one or more network interfaces 616. In some implementations, electronic system 600 may include or be integrated with other computing devices or circuitry for operation of the various components and processes previously described.

Bus 608 collectively represents all system, peripheral, and chipset buses that communicatively connect the numerous internal devices of electronic system 600. For instance, bus 608 communicatively connects processing unit(s) 612 with ROM 610, system memory 604, and permanent storage device 602.

From these various memory units, processing unit(s) 612 retrieves instructions to execute and data to process in order to execute the processes of the subject disclosure. The processing unit(s) can be a single processor or a multi-core processor in different implementations.

ROM 610 stores static data and instructions that are needed by processing unit(s) 612 and other modules of the electronic system. Permanent storage device 602, on the other hand, is a read-and-write memory device. This device is a non-volatile memory unit that stores instructions and data even when electronic system 600 is off. Some implementations of the subject disclosure use a mass-storage device (such as a magnetic or optical disk and its corresponding disk drive) as permanent storage device 602.

Other implementations use a removable storage device (such as a floppy disk, flash drive, and its corresponding disk drive) as permanent storage device 602. Like permanent storage device 602, system memory 604 is a read-and-write memory device. However, unlike storage device 602, system memory 604 is a volatile read-and-write memory, such a random access memory. System memory 604 stores some of the instructions and data that the processor needs at runtime. In some implementations, the processes of the subject disclosure are stored in system memory 604, permanent storage device 602, and/or ROM 610. From these various memory units, processing unit(s) 612 retrieves instructions to execute and data to process in order to execute the processes of some implementations.

Bus 608 also connects to input and output device interfaces 614 and 606. Input device interface 614 enables the user to communicate information and select commands to the electronic system. Input devices used with input device interface 614 include, e.g., alphanumeric keyboards and pointing devices (also called "cursor control devices"). Output device interfaces 606 enables, e.g., the display of images generated by the electronic system 600. Output devices used with output device interface 606 include, e.g., printers and display devices, such as cathode ray tubes (CRT) or liquid crystal displays (LCD). Some implementations include devices such as a touchscreen that functions as both input and output devices.

Also, as shown in FIG. 6, bus 608 also couples electronic system 600 to a network (not shown) through network interfaces 616. Network interfaces 616 may include, e.g., a wireless access point (e.g., Bluetooth or WiFi) or radio circuitry for connecting to a wireless access point. Network interfaces 616 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 600 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all implementations, or one or more implementations. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. An electronic tag, the electronic tag comprising:
a housing;
a processor within the housing;
a transceiver configured within the housing and coupled to the processor, wherein the processor is configured to send, via the transceiver, first signals to an infusion device and to receive, via the transceiver, second signals from the infusion device;
a display coupled to the housing and the processor, and configured to display information received via the transceiver;
a clamping mechanism coupled to the housing and configured to secure the electronic tag to an intravenous (IV) tubing; and
a sensor configured within the housing, and configured to measure a property of a fluid in an IV tubing at a location of the clamping mechanism, wherein the sensor comprises an acoustic sensor configured to measure acoustics within at least a portion of the IV tubing or the sensor comprises a pressure sensor configured to detect a fluidic pressure of a fluid within the IV tubing at the location of the IV tubing, and wherein the property of the fluid measured by the sensor is transmitted via the transceiver to the infusion device, and wherein the information displayed by the display is displayed in response to a control signal received via the transceiver from the infusion device.

2. The electronic tag of claim 1, wherein the processor is configured to send, via the transceiver, first signals to an infusion device and to receive, via the transceiver, second signals from the infusion device.

3. The electronic tag of claim 2, wherein the first signals sent to the infusion device is configured to trigger an alarm at a location remote to the electronic tag when a fault condition exists.

4. The electronic tag of claim 2, wherein the transceiver comprises a wireless communication device and is configured to communicate with the infusion device via a wireless connection.

5. The electronic tag of claim 1, wherein:
the processor is configured to cause the electronic tag to receive from an infusion device, through the transceiver, infusion information about a content of an IV infusion container, and infusion parameters of an infusion process associated with the IV infusion container; and
the display is configured to display the infusion information and the infusion parameters.

6. The electronic tag of claim 1, wherein the housing comprises a first elongated receptacle configured to receive a portion of the IV tubing, and the clamping mechanism comprises a clamp arm and a spring configured to apply tension to the clamp arm to restrain the portion of the IV tubing within the first elongated receptacle.

7. The electronic tag of claim 6, wherein:
the display is disposed on a first side of the housing, opposite the first elongated receptacle and the clamp arm; and
wherein the clamp arm includes a second elongated receptacle, the first elongated receptacle and the second elongated receptacle being configured to jointly surround the portion of the IV tubing to restrain at least the portion of the IV tubing between the clamp arm and the first elongated receptacle.

8. The electronic tag of claim 7, wherein the first elongated receptacle and the second elongated receptacle form a substantially cylindrical shape when the claim arm is moved to restrain the IV tubing, and wherein the sensor is disposed within the first elongated receptacle and is configured to contact the restrained IV tubing.

9. The electronic tag of claim 1, further comprising a lock to secure the electronic tag to the IV tubing.

10. The electronic tag of claim 1, further comprising at least one colored light emitting diode (LED), wherein the at least one colored LED is configured to emit a first color when a fault condition exists and to emit a second color, different from the first color, during normal operation.

11. The electronic tag of claim 1, further comprising a signal emitter configured to emit signals for associating the electronic tag with an infusion device or a second electronic tag.

12. The electronic tag of claim 11, wherein the signal emitter comprises an acoustic transducer or a pressure actuator.

13. A method of associating an intravenous (IV) infusion container to an infusion pump of an infusion device, the method comprising:
receiving, at the infusion pump, an IV tubing coupled with the IV infusion container, wherein an electronic tag is affixed to the IV tubing, wherein the electronic tag comprises:
a housing;
a processor within the housing;
a transceiver configured within the housing and coupled to the processor, wherein the processor is configured to send, via the transceiver, first signals to an infusion device and to receive, via the transceiver, second signals from the infusion device;
a display coupled to the housing and the processor, and configured to display information received via the transceiver;
a clamping mechanism coupled to the housing and configured to secure the electronic tag to an intravenous (IV) tubing; and
a sensor configured within the housing, and configured to measure a property of a fluid in an IV tubing at a location of the clamping mechanism, wherein the sensor comprises an acoustic sensor configured to measure acoustics within at least a portion of the IV tubing or the sensor comprises a pressure sensor configured to detect a fluidic pressure of a fluid within the IV tubing at the location of the IV tubing, and wherein the property of the fluid measured by the sensor is transmitted via the transceiver to the infusion device, and wherein the information displayed by the display is displayed in response to a control signal received via the transceiver from the infusion device;

causing a signal to be transmitted from at least one of the IV infusion container and the infusion pump of the infusion device;

receiving, from the electronic tag, a confirmation message indicating that the sensor of the electronic tag received an association signal;

determining that the association signal corresponds to the signal transmitted by the at least one of the IV infusion container and the infusion pump;

causing the electronic tag to display a message on the display of the electronic tag indicating an association with the IV infusion container or the infusion pump of the infusion device.

14. The method of claim 13, wherein:

causing the signal to be transmitted from the IV infusion container comprises applying a pressure to the IV infusion container; and wherein the sensor of the electronic tag comprises a pressure sensor; and wherein the confirmation message indicates that the electronic tag detected an increase in a fluidic pressure in the IV tubing caused by the pressure applied to the IV infusion container.

15. The method of claim 14, further comprising:

causing the display of the electronic tag to display an instruction for applying the pressure to the IV infusion container; and wherein said displaying of the message is based at least in part on determining that the confirmation message is received within a first time period measured from a time the instruction was displayed.

16. The method of claim 13, wherein:

transmitting the signal at the infusion pump of the infusion device comprises transmitting an acoustic signal within the IV tubing at the infusion pump of the infusion device; and wherein the sensor of the electronic tag comprises an acoustic sensor; and wherein the confirmation message indicates that the electronic tag measures a detected acoustic signal in the IV tubing caused by the acoustic signal generated at the infusion pump of the infusion device.

17. The method of claim 16, wherein:

the acoustic signal generated at the infusion pump of the infusion device comprises a modulated acoustic signal, the modulated acoustic signal is caused by variations in movements of a pump in the infusion device; and wherein the confirmation message indicates a detected modulation of the detected acoustic signal in the IV tubing, and the method further includes determining that the detected modulation of the detected acoustic signal in the IV tubing corresponds to a modulation of the modulated acoustic signal generated at the infusion pump of the infusion device.

18. A method of associating an intravenous (IV) infusion container to an infusion pump of an infusion device, the method comprising:

determining, at an electronic tag, that the electronic tag is affixed to an IV tubing coupled with the IV infusion container, wherein the electronic tag comprises:

a housing;

a processor within the housing;

a transceiver configured within the housing and coupled to the processor, wherein the processor is configured to send, via the transceiver, first signals to an infusion device and to receive, via the transceiver, second signals from the infusion device;

a display coupled to the housing and the processor, and configured to display information received via the transceiver;

a clamping mechanism coupled to the housing and configured to secure the electronic tag to an intravenous (IV) tubing; and a sensor configured within the housing, and configured to measure a property of a fluid in an IV tubing at a location of the clamping mechanism, wherein the sensor comprises an acoustic sensor configured to measure acoustics within at least a portion of the IV tubing or the sensor comprises a pressure sensor configured to detect a fluidic pressure of a fluid within the IV tubing at the location of the IV tubing, and wherein the property of the fluid measured by the sensor is transmitted via the transceiver to the infusion device, and wherein the information displayed by the display is displayed in response to a control signal received via the transceiver from the infusion device;

receiving a signal transmitted from at least one of the IV infusion container and the infusion pump of the infusion device;

generating, by the electronic tag, based on the signal, a confirmation message indicating that the sensor of the electronic tag received an association signal;

transmitting the confirmation message to the at least one of the IV infusion container and the infusion pump of the infusion device;

receiving from the IV infusion container or the infusion pump of the infusion device a message indicating association with the IV infusion container or the infusion pump of the infusion device;

causing the electronic tag to display a message on the display of the electronic tag indicating an association with the IV infusion container or the infusion pump of the infusion device.

* * * * *